United States Patent
Becker

(10) Patent No.: US 6,823,805 B2
(45) Date of Patent: Nov. 30, 2004

(54) TABLE FOR OPERATING ROOM

(76) Inventor: Dan L. Becker, 5045 Keeneland Cir., Orlando, FL (US) 32819

( * ) Notice: Subject to any disclaimer, the term of this patent is extended or adjusted under 35 U.S.C. 154(b) by 0 days.

(21) Appl. No.: 10/376,123

(22) Filed: Feb. 28, 2003

(65) Prior Publication Data

US 2003/0167979 A1 Sep. 11, 2003

Related U.S. Application Data

(60) Provisional application No. 60/361,836, filed on Mar. 5, 2002, and provisional application No. 60/418,447, filed on Oct. 15, 2002.

(51) Int. Cl.[7] .............................................. A47B 11/00
(52) U.S. Cl. ........................................ 108/103; 108/90
(58) Field of Search ........................... 150/158; 108/90, 108/141, 103, 105, 139, 92, 93, 94, 95; 280/43, 43.14; 16/44

(56) References Cited

U.S. PATENT DOCUMENTS

| | | | | |
|---|---|---|---|---|
| 2,679,890 A | * | 6/1954 | Zannoth | .................. 248/124.2 |
| 2,690,366 A | | 9/1954 | Kimmel | |
| 3,543,699 A | * | 12/1970 | Leikarts | ........................ 108/59 |
| 3,550,892 A | * | 12/1970 | Propst | ..................... 248/282.1 |
| 3,721,315 A | * | 3/1973 | Wehner | ........................ 182/15 |
| 3,747,655 A | * | 7/1973 | Hadtke | .......................... 108/90 |
| 3,998,221 A | | 12/1976 | Collins | |
| 4,122,956 A | * | 10/1978 | Hargrove | ............... 211/126.14 |
| D270,588 S | | 9/1983 | Kemple | |
| 4,687,167 A | * | 8/1987 | Skalka et al. | ................ 248/126 |
| 4,779,540 A | * | 10/1988 | Dion et al. | ..................... 108/98 |
| 4,833,972 A | | 5/1989 | Bohusch et al. | |
| 4,873,997 A | | 10/1989 | Marshall | |
| 4,927,214 A | | 5/1990 | Kaufman et al. | |
| 4,938,364 A | * | 7/1990 | Stadelman et al. | ............ 211/47 |
| 4,976,450 A | * | 12/1990 | Ellefson | .................. 280/79.11 |
| 5,116,032 A | | 5/1992 | Strachan | |
| 5,170,804 A | | 12/1992 | Glassman | |
| 5,379,703 A | * | 1/1995 | Marshall | ....................... 108/90 |
| 5,411,036 A | | 5/1995 | Wilkes | |
| 6,019,102 A | | 2/2000 | Becker | |
| 6,189,459 B1 | | 2/2001 | DeAngelis | |
| 6,283,125 B1 | | 9/2001 | McNeirney et al. | |
| 6,286,164 B1 | | 9/2001 | Lamb et al. | |
| 6,298,855 B1 | | 10/2001 | Baird | |
| 6,314,959 B1 | | 11/2001 | Griesbach et al. | |
| 6,336,412 B2 | | 1/2002 | Heimbrock et al. | |

FOREIGN PATENT DOCUMENTS

| | | |
|---|---|---|
| DE | 3442944 | 5/1986 |
| DE | 8615366 | 7/1986 |
| DE | 3913617 | 10/1990 |
| FR | 745004 | 5/1933 |
| FR | 2711507 | 5/1995 |
| GB | 1585678 | 11/1981 |

\* cited by examiner

*Primary Examiner*—Janet M. Wilkens
(74) *Attorney, Agent, or Firm*—David G. Maire

(57) ABSTRACT

A table (10) for an operating room providing a cantilevered over-patient instrument surface (12) that can be swiveled away from the operating field without moving the base (20) of the table. The instrument surface may have two levels (38, 40) with a variable degree of overlap between the levels to form an instrument surface of a desired area. The instrument surface may further have a curved edge (44) so that the proximity of the instrument surface to the operating field does not change as the instrument surface is rotated relative to its base. A sterile drape (60) covers the instrument surface and extends downward to be attached around the table support structure (14). The drape may be formed of two sections (62, 64) having overlapping tail portions (68, 70, 72, 74). The base may include a footpad (24) for a nurse (26) working at the table. Spring-loaded rollers (30) facilitate movement of the table across the floor (34) while withdrawing under the weight of a nurse standing on the footpad to provide unmoving contact between the base and the floor when the table is in use.

7 Claims, 4 Drawing Sheets

TABLE FOR OPERATING ROOM

This application claims benefit of the Mar. 5, 2002, filing date of U.S. provisional application No. 60/361,836 and the Oct. 15, 2002, filing date of U.S. provisional application No. 60/418,447.

FIELD OF THE INVENTION

This invention relates generally to the field of medical surgery, and more particularly to the field of tables for a medical operating room that are covered by a sterile drape.

BACKGROUND OF THE INVENTION

Sterile and non-sterile areas are carefully delineated in hospital operating rooms. Sterile instrument lay-down areas are needed for storing various instruments for easy access near the patient during an operation.

One type of table used in operating rooms is an over-patient table that has an instrument surface supported by four legs. Opposed legs on respective skies of the table are spaced far enough apart so that the table can span the width of an operating roam table so that the table may be positioned over a patient who is lying on the operating table. Each leg of the table is supported by a roller mechanism so that the table may be rolled Into position proximate the operating field after the patient has been placed on the operating table. Such over-patient tables are available from Pedigo Products. Inc. of Vancouver. Wash. Examples can be found on the Pedigo Products website. Other such tables are sold under the registered trademark MAYFIELD®. A sterile drape is placed over the Instrument surface and is attached to a sterile drape placed over the patient. The instrument surface is supported by the table legs at an adjustable height above the patient. Instruments positioned on the Instrument surface are handled by a nurse standing next to the table along side the operating table. Because the instrument surface must be above the patient, it is generally too high for comfortable access by the nurse standing on the floor. It is common for the nurse to use a footstool in conjunction with the MAYFIELD® table to facilitate access to the instrument surface. Such footstools are also available from Pedigo Products, Inc. and can be viewed on their web page cited above.

A second type of table used in operating rooms is known as a Mayo table. The Mayo table has an instrument surface supported by a post, which in turn is supported by two legs projecting under the instrument surface. The legs may have a generally flat bottom for stability, or they may be supported by wheels, or a combination of the two. Mayo tables are also available from Pedigo Products, Inc. and can be viewed on their web page cited above. The height of the instrument surface is changed by extending or retracting the post. A sterile drape is wrapped over the instrument surface and around the post. A nurse using the Mayo table will stand beside the table, again often using a footstool to facilitate access to the elevated instrument surface. The Mayo table is moved into position proximate the operating field once the patient has been placed on the operating table by rolling or dragging it across the floor.

A Mayo table provides an instrument surface beside an operating table. Operating tables generally have large, sturdy bases that extend to the full width of the table top. The base of the operating table prevents a Mayo table from being positioned over the patient. Over-patient instrument storage can only be provided by a MAYFIELD® table.

It is often necessary to perform an X-ray examination of the patient during an operation. To accomplish such an intra-operatlve X-ray, any instrument table located proximate the operating field must be temporarily removed to provide room for positioning the X-ray equipment over the patient. Intra-operative movement of a MAYFIELD® table is very difficult and is generally avoided because the sterile drape covering a MAYFIELD® table is generally attached to a sterile drape covering the patient. Intra-operative movement of a Mayo table can be accomplished by pulling the table away from the operating table, then pulling it back into position after completion of the X-ray examination. Thus, in any operation that is expected to involve an X-ray examination, the use of a MAYFIELD® table and its convenient over-patient instrument surface is often avoided, leaving the surgical team with only the Mayo table option for instrument storage.

SUMMARY OF THE INVENTION

A table having improved functionality in an operating room environment is described. The table allows an instrument surface to be located in an over-patient position without positioning the table base under the operating table. The table further allows the instrument surface to be rotated away from the over-patient position without relocating its base. A footpad is integrated with the table structure to provide access to the instrument surface, thereby better utilizing the available space around an operating table. Selective positioning of overlapping upper and lower instrument surface tiers will change the area of the instrument surface. The table is covered with a drape that ensures that the entire instrument surface area remains sterile even when the upper and lower surface tiers are re-positioned.

A table for an operating room is describe herein as including an instrument surface upper tier and an instrument surface lower tier moveable to a desired degree of overlap there between to define a desired area of instrument storage space. The table may include an upper drape enveloping the instrument surface upper tier; and a lower drape disposed over at least a top surface of the instrument surface lower tier. A table for an operating room is describe as including: an instrument surface; a support structure for supporting the instrument surface at a height above a floor; and a swivel connection between the instrument surface and the support structure allowing the instrument surface to be rotated in a horizontal plane relative to the support structure. The table may include a drape disposed over the instrument surface.

A table for an operating room is described as including a support structure and an instrument surface connected to the support structure and extending horizontally beyond the support structure in cantilever fashion so that the instrument surface extends to an over-patient position when the support structure is positioned beside an operating table.

DETAILED DESCRIPTION OF THE INVENTION

Figure 1:
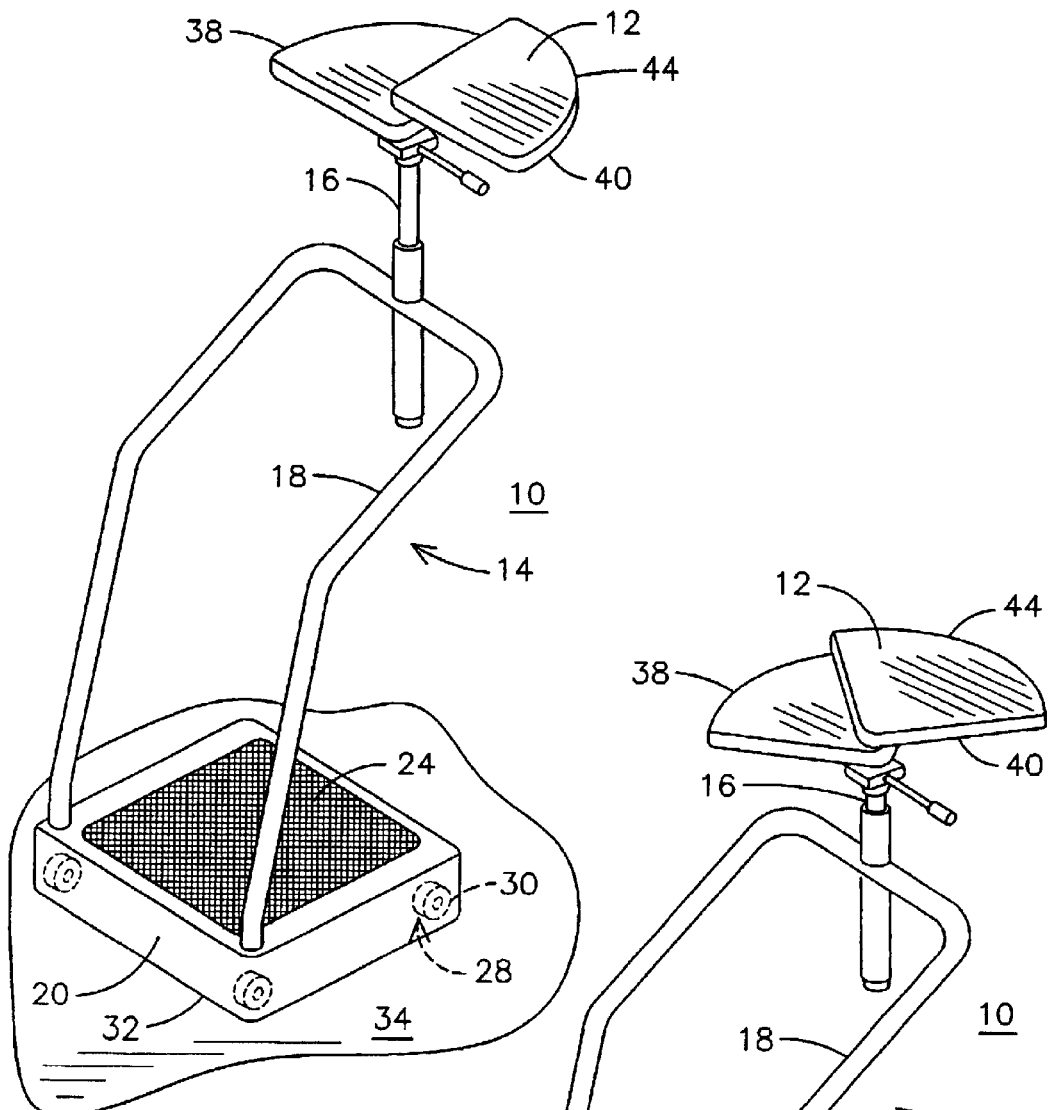
FIG. 1 is a perspective view of a table for an operating room with its instrument surface in a fully extended position and shown without a sterile drape.
Figure 2:
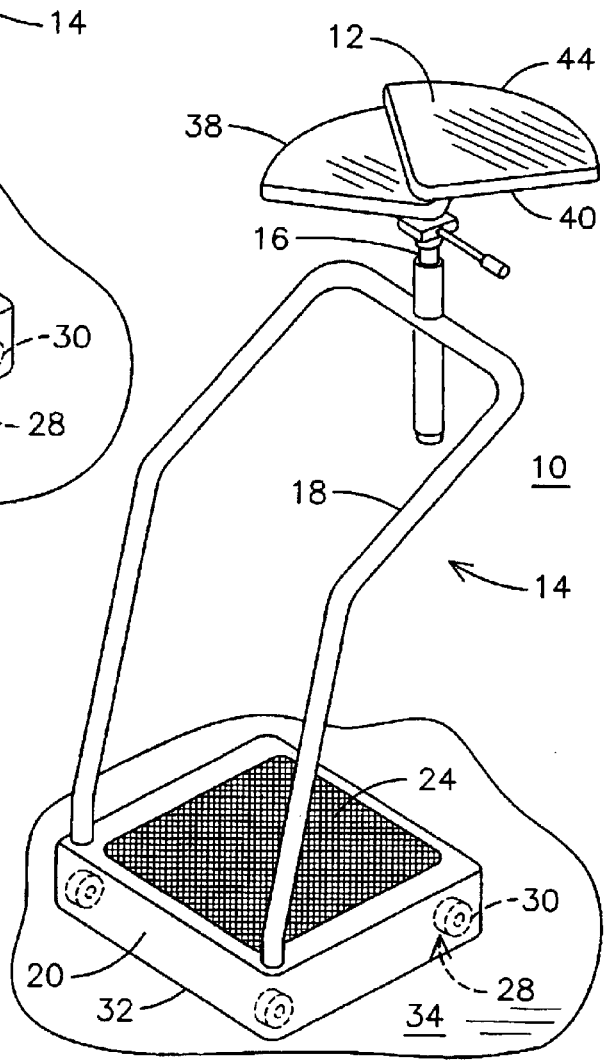
FIG. 2 is a perspective view of the table of FIG. 1 with its instrument surface in a side position.

An improved table 10 for an operating room environment is illustrated in FIGS. 1–4. The table has an instrument surface 12 usable for storing the various instruments that are needed during a surgical operation. The term "instrument surface" is meant to encompass the three-dimensional object not just the two-dimensional top plane. The instrument surface 12 may be formed from one or more plates of stainless steel or other material suitable for a hospital operating room environment. The instrument surface 12 may be completely flat on top, or it may have an upwardly curved edge, or it may contain specifically formed depressions for better retaining particular objects. The instrument surface 12 is supported above the floor 34 by a support structure 14 including a post 16, two legs 18 and a base 20. Other designs of support structures may be envisioned having a generally vertically extending portion to provide a desired height and a base component for contacting the supporting surface. The support structure 12 provides sufficient structure stability for reliably holding objects placed on the instrument surface 12. Components of the support structure 14 may be formed of stainless steel, aluminum or other material suitable for the operating room environment. The post 16 may include a spring-biased pneumatic actuator for adjustment to a plurality of lengths so that the height of the instrument surface 12 above the floor may be selected to accommodate various use applications. A hand or foot release mechanism may be used for such an actuator. FIG. 1 illustrates the post 16 in a fully extended position and FIG. 2 illustrates the post 16 in a retracted position. In one embodiment, the instrument surface 12 may be adjusted in a range of 40–50 inches above the floor. One may appreciate that the support structure 14 may take other shapes, such as with one or more legs, fixed or variable height post, no separate post, rectangular base or base with two or more extending feet, etc.

The instrument surface 12 is supported in cantilever fashion by the support structure 14. This allows the instrument surface to extend horizontally beyond the base 20 to an over-patient position when the support structure 14 is placed beside an operating table 22. One embodiment may provide approximately 16.5 inches of horizontal extension beyond the edge of the base 20 to extend over the patient when being used. Other embodiments may extend horizontally beyond the base 20 in cantilever fashion by at least 10 inches or 12 inches or 14 inches or to a particular distance that is useful to place the instrument surface 12 within the operating field and/or over the patient with a particular operating table design. This is particularly useful for operating tables having a solid base structure that does not permit a table base to be extended under the patient lay down area. The dimensions and weight of the table component parts are selected to support a predetermined amount of weight, for example 40 or 50 pounds, on the instrument surface 12 without danger of toppling of the table 10. The use of the table 10 must be controlled so that the design weight limit is not exceeded.

Figure 4:
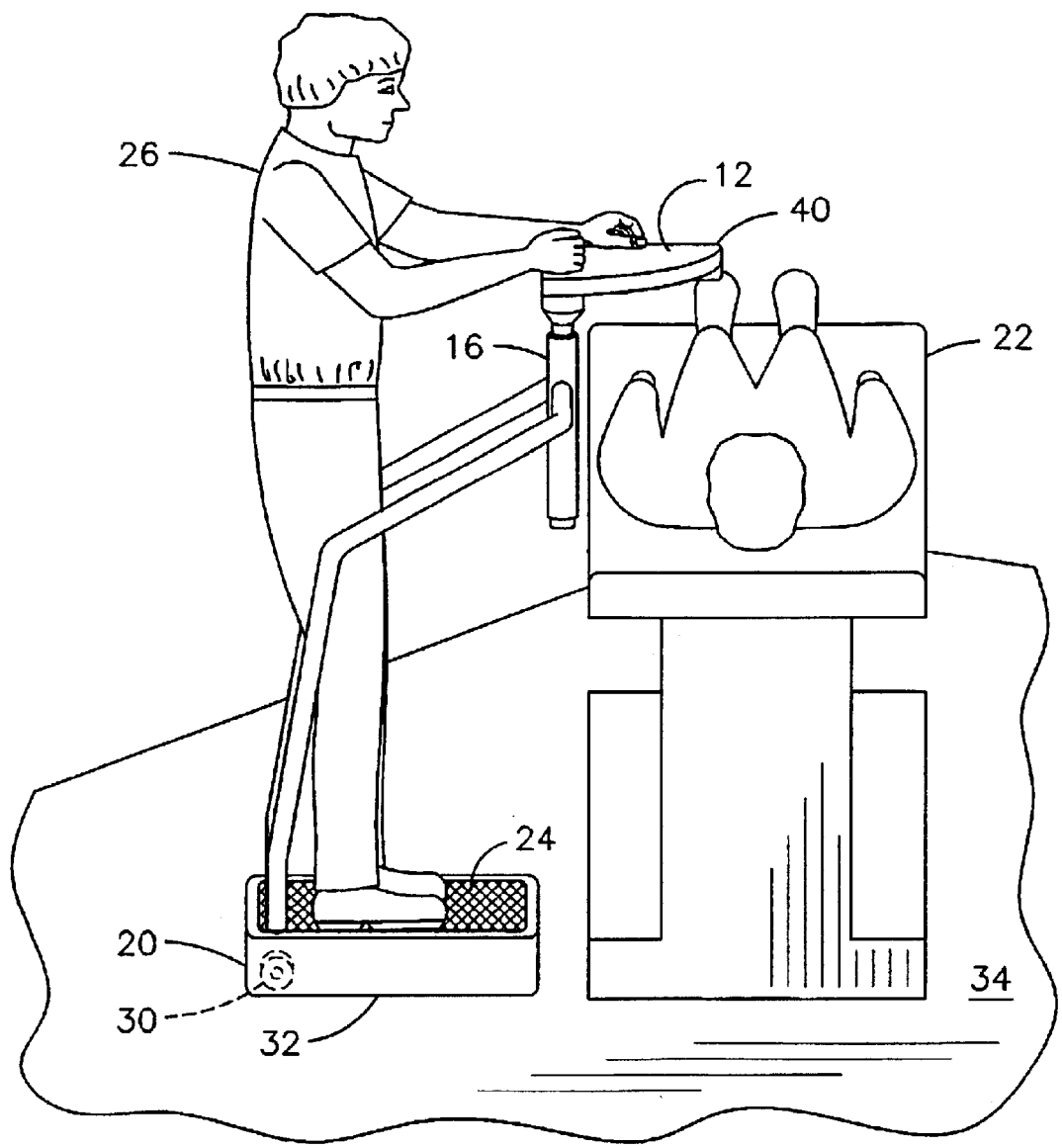
FIG. 4 is a perspective view of the table of FIG. 1 being used in an operating room.

A footpad 24 is formed on a top surface of the base 20. The footpad 24 is illustrated as a section of non-slip material attached to a generally planar top surface of the base 20. Other embodiments having a footpad associated with the support structure 14 may be envisioned. Examples include: a generally planar metal member having a roughened surface connected between two legs of a generally V-shaped base; two individual foot structures connected to the base or to respective legs of the support structure; and a top surface of the base having an area large enough for a person to stand upon, with or without a special no-slip finish. A nurse 26 using the table 10 may stand on the footpad 24, as illustrated in FIG. 4. The footpad 24 not only positions the nurse 26 at a convenient location relative to the instrument surface, but it also provides a desired step upward to facilitate access to the elevated instrument surface 12. Thus, the footpad 24 allows the nurse 26 to work at the table 10 rather than beside it. This reduces the amount of room around the operating table 22 that is required for the table 10 and the nurse 26, thereby freeing valuable space for other equipment or for the improved comfort of the surgical team. The footpad 24 also eliminates the need for the separate footstool that was used with the prior art Mayo and Mayfield tables. Alternatively, if additional foot height is desired, a separate removable footstool (not shown) may be placed on top of the footpad 24. The footpad 24 may further be used for storing such footstools or other equipment when the table 10 is not in use.

The table 10 is supported on four roller mechanisms 28 attached to respective corners of the bottom of the base 20. The roller mechanisms 28 may be casters, wheels, or other such mechanisms known in the art, and they may be spring-biased downward. A roller 30 portion of the roller mechanism 28 is spring-loaded to extend beyond the bottom surface of the base 20. The number and placement of such roller mechanisms 28 may vary to accommodate various geometries of the base 20. The spring coefficient of the roller mechanism 28 is selected so that the roller 30 extends below the bottom of the base 20 for supporting the table 10 on the roller 30 when the footpad 24 is clear. This allows the table 10 to be moved across the floor easily. The spring coefficient is further selected so that the roller 30 moves to a withdrawn position allowing the base bottom surface 32 to make unmoving contact with the floor 34 under the weight of a person 26 standing on the footpad 24, as illustrated in FIG. 4. Alternatively, if the roller mechanism 28 is not spring-biased and the rollers or wheels remain extended at all times, the mechanism 28 may have some form of releasable braking device that allows the roller 30 to be locked into a fixed position once the table 10 is located in a desired position on the floor 34.

Figure 3:
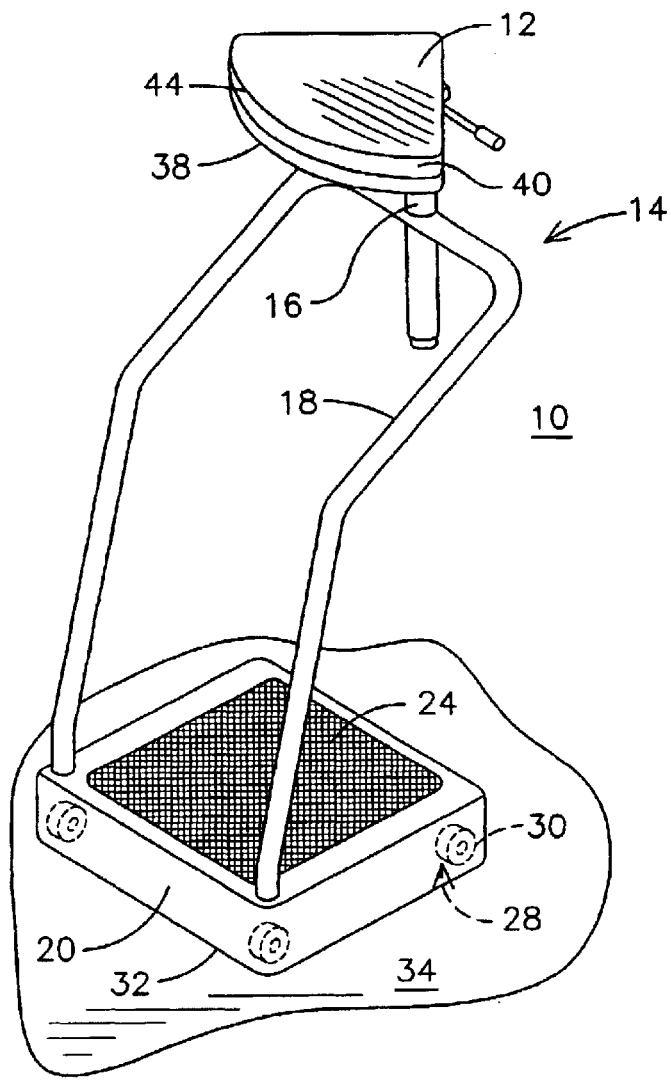
FIG. 3 is a perspective view of the table of FIG. 1 with its instrument surface in a storage position.
Figure 5:
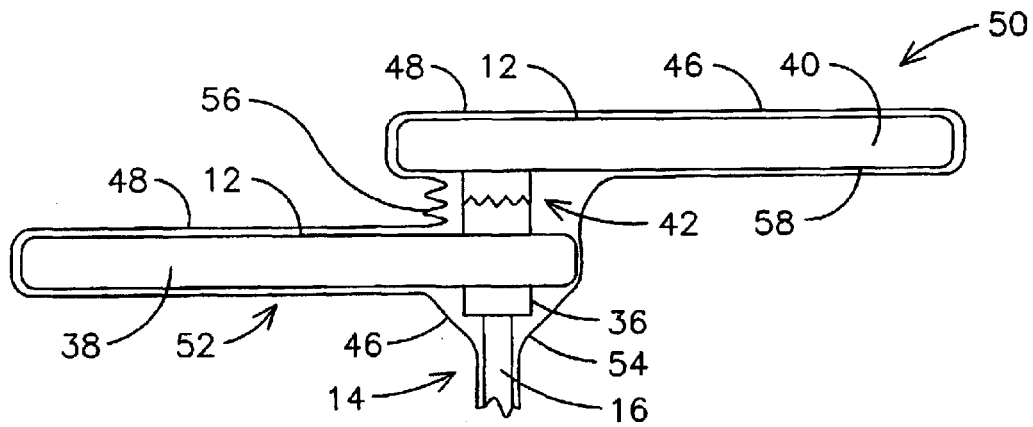
FIG. 5 is a partial side view of the table of FIG. 1 covered by a one-piece sterile drape.

The instrument surface 12 is connected to the support structure 14 by a swivel connection 36, seen best in FIG. 5, to allow the instrument surface 12 be rotated in a horizontal plane relative to the support structure 14. FIG. 1 illustrates the instrument surface 12 in an over-patient position and FIG. 3 illustrates the instrument surface 12 in a storage position directly over the base 20. The swivel connection 36 may utilize a hinge, bearings, low-friction materials, etc. to provide the desired degree of rotational freedom. A releasable locking mechanism may be included to hold the instrument surface at a desired angular position relative to the support structure. The instrument surface 12 may thus be moved between, and may be locked at, any of a plurality of vertical and angular positions relative to the post 16. Alternatively, the instrument surface 12 may be free to rotate without a locking mechanism, perhaps with a degree of friction being designed into the swivel connection to require a predetermined amount of force to rotate the instrument surface 12. This feature is especially useful when the table is being used during a surgical procedure that requires an X-ray machine to be moved into the operating field or that otherwise requires repositioning of the instrument surface 12. By simply rotating the instrument surface 12 away from the operating field, improved access may be provided to the operating field without the need for moving the base 20 of the table 10. If additional room is needed, the table 10 may be rolled across the floor 34 to a position remote from the operating table 22.

Instrument surface 12 may be formed in two tiers by a lower tier generally planar member 38 and an overlapping upper tier generally planar member 40. The lower tier generally planar member 38 and the upper tier generally planar member 40 are separated by a swivel joint to be horizontally moveable relative to each other to vary the degree of overlap there between, such as being individually rotatable about a common shaft (not shown) or by having one tier fixed relative to the post 16 and one tier rotatable relative to the post 16. A change in the degree of overlap will vary the size of the instrument surface. FIGS. 1, 2 and 3 illustrate the instrument surface 12 having a maximum, an intermediate and a minimum size respectively. In one embodiment, the upper tier 40 must be lifted upward and away from the lower tier 38 to allow it to be rotated relative to the lower tier 38. Once moved to a desired position, the upper tier 40 is then lower toward the lower tier 40, thus engaging a locking mechanism 42 that maintains the relative angular positions of the upper and lower members. The locking mechanism 42 may have a plurality of pre-set angles in which the two members may be locked, varying from a full overlap position as illustrated in FIG. 3 to a full-width position illustrated in FIG. 1. The locking mechanism 42 is illustrated in FIG. 5 as mating teeth formed on shaft sleeves connected to the respective tiers 38, 40. Other embodiments may use a detent apparatus, a locking pin, a friction engagement, etc. The ability to change the degree of overlap and the ability to rotate the instrument surface 12 relative to the support structure 14 allow the table 10 to be configured for optimal functionality and convenience in a variety of surgical arrangements.

Instrument surface 12 may be formed to have a curved edge 44 generally concentric with a pivotal axis of the swivel connection 36. The curved edge 44 allows the angular position of the instrument surface 12 to be changed without changing the proximity of the instrument surface 12 to the operating field.

An important feature for any operating room table is the ability to apply a sterile drape to the table. Surgical drapes are well known in the art and are formed of a liquid-impervious material, for example polyethylene. It is also known to form a drape from a laminate of a liquid-impervious material and an absorptive cloth material. FIG. 5 illustrates a drape 46 applied to the table 10. The drape 46 is formed to fit generally closely against the instrument surface 12 of the table 10, so that during a surgical procedure, the sterile upper surface 48 of the drape 46 functions as the instrument lay down area. The drape 46 is formed to fit the instrument surface 12, including curved edge 44. The drape 46 includes a top tier section 48 enveloping both the upper and the lower surfaces of the upper tier 40 and a bottom tier section 50 enveloping both the upper and the lower surfaces of the lower tier 38. Alternatively, at least the upper surface of the lower tier 38 should be covered by the drape 46 to ensure that the entire instrument surface 12 remains as a sterile field. The drape 46 also includes a portion 54 extending downward from the instrument surface 12 for covering at least a portion of the support structure 14. The drape 46 may be sized or tied to fit generally closely to the post 16 without binding on the post 16 so that it is free to rotate as the instrument surface 12 is rotated relative to the base 20 of the table 10.

The drape 46 may also include an expansion section 56 to accommodate relative movement between the two tiers 38, 40 of the instrument surface 12 without damage to any portion of the drape 46. Such relative movement may occur when the size of the instrument surface 12 is changed by adjusting the degree of overlap between the lower tier 38 and the upper tier 40. The expansion section 56 may be a folded, elastic or slack area that can accommodate the twisting motion imposed on the drape 46. The two sections 50, 52 of the drape 46 are moveable relative to each other as the degree of overlap between the upper and lower members is adjusted. Importantly the underside 58 of the upper tier 40 is covered by the drape so that the sterile condition of the instrument surface 12 is maintained as the overlap between the upper and lower tiers 50, 52 is changed. This allows the size of the instrument surface 12 to be changed after the sterile drape 46 is applied to the table 10.

Figure 6:
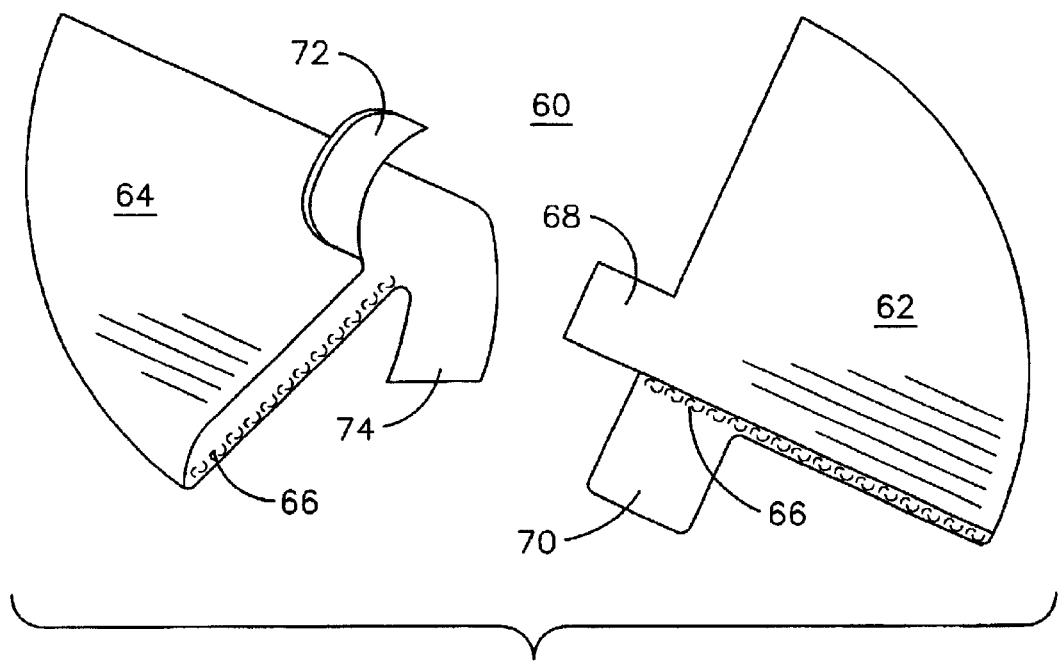
FIG. 6 is a perspective view of a two-piece sterile drape for the table of FIG. 1.

FIG. 6 illustrates a two-piece sterile drape 60 for use with two-tiered table 10. The two-piece drape 60 has two sections 62, 64 that are formed to envelope the respective tiers 38, 40 of the table with a snug fit, with one edge of each section 38, 40 being open but sealable for inserting the table tier 38, 40 into the drape section 63, 64. The resealable seam may use a hook and loop fastener 66 such as a VELCRO® brand fastener. Each of the drape sections 62, 84 also includes respective upper and lower tall portions 68, 70, 72, 74 that extend beyond the portions of the drape 60 that cover the respective tiers 38, 40. These tail portions 68, 70, 72, 74 serve to cover the joint between the table tiers 38, 40 and to cover the table post 16.

To install drape 60 the upper and lower tiers 38, 40 are placed into a position wherein they are somewhat separated from each other to facilitate the draping of the table 10. The upper surface of the upper tier 40 and the underside surface of the upper tail 68 of the lower drape section 62 have a mating hook and loop fastener pair (not shown) that are joined when the lower drape section 62 is slid onto the lower table tier 38. This fastener pair serves to hold the lower drape section 62 in position during the draping activity and during the use of the draped table 10. Once the lower drape section 62 is positioned onto the table lower tier 38 and after the fastener pair is connected, the open end of the lower drape section 62 is sealed to envelope and encase the lower table tier 38. The lower tail portion 70 of the lower drape portion 62 is thus positioned proximate the table post 16 awaiting further engagement with the upper drape tail portions 72, 74.

The upper drape section 64 is then slid onto the upper table tier 40 with the top sheet of that drape covering the upper tail portion 68 of the lower section 62 that was previously attached to the table upper tier surface. This overlap prevents material from dropping between the two drape sections 62, 64 onto the connection 42 between the tiers 38, 40. The upper tail portion 72 of the upper drape 64 now hangs downward over the edge of the table upper tier 40 on generally the opposite side of the post 16 from the position of the lower tail portion 70 of the lower drape section 62.

To completely encase the post 16, the lower tail portion 74 of the upper drape 64, which may be somewhat longer than the lower tail portion 70 of the lower drape 62 and the upper tail portion 72 of the upper drape 64, is then wrapped loosely but completely around the post 16 to encompass the post 16, the lower tail portion 70 of the lower drape 62 and the upper tail portion 72 of the upper drape 64. The lower tail portion 74 of the upper drape 64 may be held in this position with a tie, wrap, hook and loop fastener, or other suitable means for keeping it in position to surround the post 16 without causing binding when the instrument surface 12 is rotated with respect to the table base 20. The overlapping interaction of the tail portions 68, 70, 72, 74 of the drape 60 ensures that both of the table tiers 38, 40, the swivel connection locking mechanism 42 and the post 16 are adequately covered by the sterile drape material even when the table tiers 38, 40 are moved with respect to each other or when the entire instrument surface 12 is rotated with respect to the base 20.

The above-described draping process places the lower drape section 62 onto the table 10 first. Alternatively, a similar draping process may be used if an upper drape is placed onto the upper tier 40 before a lower drape is placed onto the lower tier 40. Regardless of the order of the draping process, tail portions of the drape serve to extend the sterile surface around the connection between the tiers 38, 40 and post 16 in a manner that allows the table tiers 38, 40 to be rotated together with respect to the base 20 and/or with respect to each other.

Figure 7:
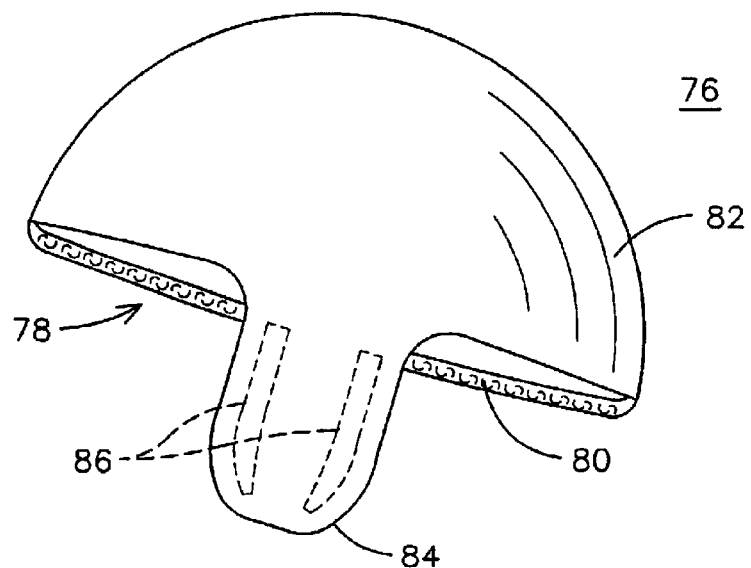
FIG. 7 is a perspective view of a one-piece sterile drape for use with the table of FIG. 1.

If the two tiers 38, 40 of table 10 are used only in the full semicircle position, or alternatively if a single tier table is provided having a swivel connection between the instrument surface and the supporting post, the drape 76 of FIG. 7 may be used to ensure that the instrument surface 12 and post 16 remain covered as the instrument surface 12 is rotated. The drape 76 is formed to snugly envelope the table instrument surface 12 with one end 78 open for installing the drape 76 onto the table 10. The open end 78 is selectively sealable such as with a hook and loop fastener 80. The upper sheet 82 of the drape 76 extends to form a tail 84 that hangs over the edge of the instrument surface generally along the post 16 of the table 10. The tail 84 is formed large enough to wrap completely around the swivel connection between the post 16 and the instrument surface 12. The tail 84 may include a hook and loop fastener mating pair 86 on its underside surface or a separate fastener may be provided so that the tail 86 may be wrapped loosely around the post 16 to provide coverage while permitting rotation of the drape 76 and instrument surface 12 relative to the post 16.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

I claim as my invention:

1. A table for an operating room, the table comprising:
   an instrument surface;
   a sterile drape covering both a top surface and an underneath surface of the instrument surface;
   a support structure for supporting the draped instrument surface at a height above a floor; and
   a swivel connection between the draped instrument surface and the support structure allowing the draped instrument surface to be rotated in a horizontal plane into and out of an over-patient position above an operating table without moving the support structure when the support structure is located adjacent the operating table;
   wherein the instrument surface further comprises a lower tier and an overlapping upper tier each rotatable in the horizontal plane about a common axis, the lower tier and the upper tier rotatable relative to each other to vary a degree of overlap there between in order to change a surface area of the top surface of the draped instrument surface.

2. The table of claim 1, the drape further comprising an upper tier section enveloping the upper tier and a lower tier section enveloping the lower tier to maintain the instrument surface as sterile when the degree of overlap is varied.

3. The table of claim 1, wherein the instrument surface comprises a curved edge generally concentric with a pivotal axis of the swivel connection.

4. A table for an operating room, the table comprising:
   an instrument surface comprising an upper tier and a lower tier adjustable to a varying degree of overlap there between;
   a sterile drape covering the instrument surface throughout the varying degree of overlap; and
   a support structure for supporting the draped instrument surface at a height above a floor.

5. The table of claim 4, further comprising a swivel connection between the instrument surface and the support structure allowing the draped instrument surface to be rotated into and out of an over-patient position above an operating table without moving a base of the support structure when the base is located on the floor adjacent the operating table.

6. The table of claim 4, the sterile drape further comprising an upper tier section enveloping the upper tier and a lower tier section enveloping the lower tier to maintain the instrument surface as sterile when the degree of overlap is varied.

7. The table of claim 4, wherein the support structure comprises a footpad where a person may stand to access the instrument surface.

* * * * *